(12) United States Patent
Thomson et al.

(10) Patent No.: US 7,611,852 B2
(45) Date of Patent: Nov. 3, 2009

(54) FUNCTIONAL CARDIOMYOCYTES FROM HUMAN EMBRYONIC STEM CELLS

(75) Inventors: James A. Thomson, Madison, WI (US); Timothy J. Kamp, Madison, WI (US); Yue Ma, Madison, WI (US); Jia-Qiang He, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 278 days.

(21) Appl. No.: 10/627,245

(22) Filed: Jul. 25, 2003

(65) Prior Publication Data

US 2004/0106095 A1 Jun. 3, 2004

Related U.S. Application Data

(60) Provisional application No. 60/399,330, filed on Jul. 26, 2002.

(51) Int. Cl.
*G01N 33/567* (2006.01)
*C12N 5/08* (2006.01)
*C12N 5/00* (2006.01)
*C12N 5/02* (2006.01)

(52) U.S. Cl. ............... 435/7.21; 435/366; 435/375; 435/377

(58) Field of Classification Search ........... 435/7.21, 435/366, 375, 377
See application file for complete search history.

(56) References Cited

U.S. PATENT DOCUMENTS

| | | | |
|---|---|---|---|
| 5,928,943 | A | 7/1999 | Franz et al. |
| 2002/0092035 | A1 | 7/2002 | Hescheler |
| 2003/0232431 | A1 | 12/2003 | Law |
| 2005/0037489 | A1* | 2/2005 | Gepstein et al. ............ 435/366 |

FOREIGN PATENT DOCUMENTS

| | | |
|---|---|---|
| DE | 198 43 234 A1 | 3/2000 |
| EP | 198 43 234 A1 | 3/2003 |

OTHER PUBLICATIONS

U.S. Appl. No. 60/306,462.*

Bosch et a. Effects of the chromanol 293B, a selective blocker of the slow, component ofthe delayed rectifier K+ current, on repolarization in human and guinea pig ventricular myocytes.Cardiovasc Res. May 1998;38(2):441-50.*
Carlsson et al. Electrophysiological characterization of the prokinetic agents cisapride and mosapride in vivo and in vitro: implications for proarrhythmic potential?J Pharmacol Exp Ther. Jul. 1997;282(1):220-7.*
Li et al. Evidence for two components of delayed rectifier K+ current in human ventricular myocytes. Circ Res. Apr. 1996;78(4):689-96.*
Priori et al. (1996) Circ. Res. 78:1009-1015.*
Bauwens, CI et al, 2008, Control of human embryonic stem cell colony and aggregate size heterogeneity influences differentiation trajectories, Stem Cells, 26:2300-2310.*
Burridge, PW et al, 2007, Improved human embryonic stem cell embryoid body homogeneity and cardiomyocyte differentiation from a novel V-96 plate aggregation system highlights interline variability, 25:929-938.*
Gryshchenko, O., et al., "Role of ATP-dependent K+ channels in the electrical excitability of early embryonic stem . . . ," Journal of Cell Science 112:2903-2912 (1999).
He, J-Q, et al., "Human Embryonic Stem Cells Develop into Multiple Types of Cardiac Myocytes: Action Potential Characterization," Circ. Res. 93:32-39 (2003).
Kolossov, E., et al., "Functional Characteristics of ES Cell-derived Cardiac Precursor Cells Identified by Tissue-specific Expression . . . ," J. of Cell Biol. 143:2045-2056 (1998).
Maltsev, V.A., et al., "Embryonic stem cells differentiate in vitro into cardiomyocytes representing sinusnodal, atrial . . . ," Mechanisms of Development 44:41-50 (1993).
Maltsev, V.A., et al., Cardiomyocytes Differentiated In Vitro From Embryonic Stem Cells Developmentally Express . . . , Circulation Research 75:233-244 (1994).
Maltsev, V.A., et al., "Establishment of beta-Adrenergic Modulation of L-Type Ca2+ Current in the Early Stages . . . ," Circulation Research 84:136-145 (1999).

* cited by examiner

*Primary Examiner*—Valarie Bertoglio
(74) *Attorney, Agent, or Firm*—Quarles & Brady LLP

(57) ABSTRACT

Human embryonic stem cells form embryoid bodies in culture which contain differentiated human cells. Some of the human cells in embryoid bodies differentiate into cardiomyocytes. Here the biological and electrical characteristics of those cardiomyocytes are described with reference to the use of cardiomyocytes derived from human embryonic stem cells in drug screening protocols for mechanisms of cardiac toxicity.

5 Claims, 5 Drawing Sheets

US 7,611,852 B2

FUNCTIONAL CARDIOMYOCYTES FROM HUMAN EMBRYONIC STEM CELLS

CROSS-REFERENCE TO RELATED APPLICATION

This application claims priority from U.S. provisional patent application Ser. No. 60/399,330 filed Jul. 26, 2002.

STATEMENT REGARDING FEDERALLY SPONSORED RESEARCH OR DEVELOPMENT

This invention was made with United States government support awarded by the following agencies:

NIH HL47053

The United States has certain rights in this invention.

BACKGROUND OF THE INVENTION

Human embryonic stem cells are human cells, that may be stably multiplied and cultured in vitro, that are at least pluripotent and may be totipotent. By that it is meant that the cells can differentiate into many different mature differentiated cell types of the human body and may, in fact, be able to differentiate into all of the cell types of an adult human body. Human embryonic stem cells are created from embryonic tissues and serially cultivated thereafter in an in vitro culture.

In cultivation, human embryonic stem cells are normally maintained in an undifferentiated state by culturing in conjunction with certain factors. Notably, the cultivation of human embryonic stem cells upon fibroblasts feeder layers, or in the presence of factors derived from fibroblasts, maintain the stem cells in an undifferentiated state. With the fibroblasts or the factors from the fibroblasts removed, human embryonic stem cells can and will begin to spontaneously differentiate into a variety of tissue types. Among the intermediate structures formed by stem cells in the process of spontaneous differentiation into a variety of tissue types is a structure known as an embryoid body. Embryoid bodies begin as aggregates formed in the culture of embryonic stem cells. While culture conditions and cell line identity influence the rate formation of embryoid bodies, under many conditions, embryoid bodies will both spontaneously arise and spontaneously begin to differentiate into a variety of different tissue types.

Among the tissue types present in embryoid bodies are known to be cardiomyocytes. These early cardiomyocytes are the precursors of human adult cardiac cells. Adult cardiomyocytes permanently withdraw from the cell cycle and cannot regenerate. The fact that cardiomyocytes were among the cells present in the embryoid bodies formed by stem cells was evident by the fact that parts of the embryoid bodies will sometimes exhibit regular heartbeat-like contractions. Thus it has been previously demonstrated that human embryonic stem cells will differentiate into cells which have some of the functional properties of cardiomyocytes. Exactly what form those cardiomyocytes take, and how mature they are in their differentiation, was previously unknown. Also unknown was what electromechanical mechanisms are active in the cardiomyocytes present in embryoid bodies and what sorts of analysis of the behavior of those cardiomyocytes cells derived from stem cells can be performed.

BRIEF DESCRIPTION OF THE DRAWING FIGURES

Figure 5:
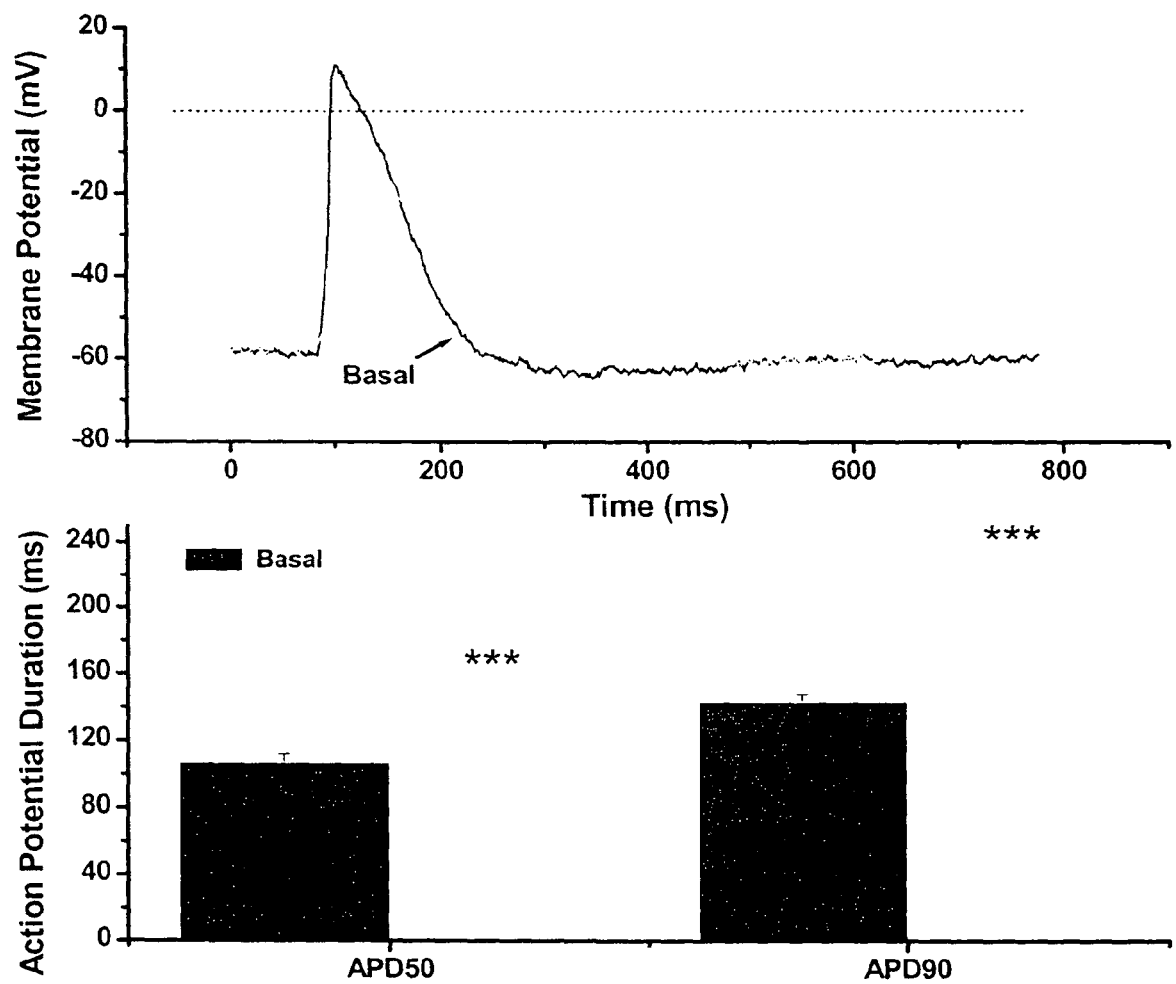

FIG. 5 presented data from the ADP study referred to in the examples below.

DETAILED DESCRIPTION OF THE INVENTION

It is described here for the first time that cardiomyocytes derived from human embryonic stem cells formed in embryoid bodies differentiate into all of the major cardiac muscle cell types, including ventricular, atrial, and nodal cells. While not all embryoid bodies will contain cardiomyocytes, those embryoid bodies which do contain cardiomyocytes will spontaneously beat. It is also disclosed herein that the beat of such cardiomyocytes can be controlled and monitored, which permits analysis of the magnitude of such beats to measure the responsiveness of the cardiac cells in culture to defined changes in environment and conditions. Monitoring the electrical potentials of individual cells in an embryoid body can reveal the nature of individual cardiomyocytes in the embryoid body and can be used to test the response of such cells to external stimuli, such as potentially toxic or therapeutic agents. In particular, it has been found that it is possible to evaluate the effect of chemicals on the HERG potassium channel of cardiac cells, and thereby test in vitro the actual effect of drugs on human heart cells in a manner that has heretofore not been possible.

The electrical activity of a cardiac cell is best characterized with reference to its action potential. The action potential is a chart of the transmembrane electrical potential, from the interior of the cardiomyocytes to the environment, which is measured over time. The action potential of various types of mature and primitive cardiac cells are different from those of other types. Here it is demonstrated that all three main classes of action potentials, nodal-like, embryonic atrial-like, and embryonic ventricular-like, can be observed in cardiomyocytes formed by human embryonic stem cells. Impaling individual beating outgrowths revealed reproducible action potential morphologies recorded from cells suggesting that each outgrowth, or embryoid body, is composed of a predominant cell type.

It has been demonstrated previously that one can find cardiomyocytes in embryoid bodies formed from human embryonic stem cells. The differentiation of human embryonic stem cells into a variety of tissue types within the body is most commonly done through the formation of what are known as embryoid bodies, referred to here as EBs. EBs are aggregations of cells which begins as irregular clumps found in the cultivated cultures of embryonic stem cells that begin to exhibit differentiated tissue types within their structure. Some embryoid bodies will spontaneously beat, suggesting the presence of cardiomyocyte-type behavior. Previous studies using immunostaining techniques on fixed cells showed the presence of cardiac-specific proteins in EBs from human embryonic stem cells. Extracellular recordings of electrical activity from aggregates of cells have supported the notion that spontaneously electrically active hearts cells are present in the EBs, but these recordings cannot provide information as to the types of cardiomyocytes present in the EBs, as the measures potentials were an average of 1 many cells present in the area of the extracellular electrode. There are a variety of techniques which can give rise to embryoid body formation, and the method used can result in a greater or lesser percentage of embryoid bodies which do contain cardiomyocytes and the types of cardiomyocytes formed has been previously uncharacterized. Thus while it has been previously shown that cardiomyocytes are formed in EBs, the type of cardiomyocytes, the capabilities of these cells, and accessibility of these cells to intracellular electrophysiological recordings have previously not been demonstrated. It is described here that the major cell types of mature heart muscle, including ventricular, atrial, and nodal cells can all be found within embryoid bodies formed from embryonic stem cells.

The cultivation of cardiomyocytes from human embryonic stem cells permits simple studies of human cardiac cell characteristics to be conducted in vitro. At the simplest level, it is possible to culture an EB that contains cardiomyocytes in a vessel or culture container and observe the pulsation or beating of that embryoid body. While not all embryoid bodies will form cardiomyocytes and exhibit pulsing or beating behavior, those embryoid bodies that do rhythmically pulse will be found to contain cardiomyocyte cells within them. At a more sophisticated level, described in greater detail below, the various embryonic cardiac cell types can separately have their action potentials taken and then the variations in action potentials can be observed following various chemical, electrical or physical perturbations of the cells.

The examples described below used cardiomyocytes derived from human embryonic stem cells which produced embryoid bodies maintained in culture 40-95 days. This is the stage at which we found heterogeneity of action potential morphologies. While action potentials with characteristics of atrial and ventricular myocytes were observed, the relatively positive MDP (−50 to 60 mV) and the slow action potential upstroke (5-30 V/sec) contrasts with neonatal and adult human atrial and ventricular cardiomyocytes which have resting membrane potentials in the range of −80 mV and $dV/dt_{max}$ ranging from 150 to 350 V/s.18 The stem cell-derived cardiomyocytes likely correlate with the "intermediate" stage described for the murine stem cell system. The limited data available describing the action potential in human embryonic and fetal hearts suggests that by 7 to 8 weeks of development the resting membrane potential and $dV/dt_{max}$ of atrial and ventricular myocytes reaches that of adult cells. Thus we referred to the atrial and ventricular action potentials observed in this study as embryonic because they have properties of the action potentials anticipated in human embryos prior to 7 weeks of development. The nodal type action potentials observed were simply described as nodal because this action potential morphology shows little change during development. This strikingly slow in vitro development of action potential properties compared to the mouse system is likely related to the markedly different gestational periods comparing mice and man.

It has been assumed that since enzymatic dissociation of a collection of embryoid body outgrowths has yielded diverse cardiomyocyte cell types, that each outgrowth is composed of a heterogeneous mix of cardiomyocytes, perhaps in part mimicking the heterogeneous collection of myocytes in the developing heart. However, the current intracellular recording of action potentials with sharp microelectrodes were unique in that repeated distinct cellular measurements were made from individual outgrowths, and we found that each outgrowth is populated by a predominant cell type. Thus we postulate that each outgrowth responds to its unique microenvironment resulting in differentiation and proliferation of one predominant type of cardiac cell.

One characteristic property of the intact heart or certain cardiomyocyte cell types is an intrinsic or spontaneous beating rate. Cells that set the beating rate are sometimes referred to as pacemaker cells. The cardiomyocytes present in EBs exhibit a spontaneous beating or contraction characterized by particular patterns of activity (episodic as opposed to continuous) as well as a frequency of beating. By either measuring directly action potentials as above or by measuring time or amplitude of cell contractions, it is possible to characterize the effect of drugs or other interventions on the spontaneous beating rate and patterns of the cardiomyocytes in culture. Agents that increase or decrease the rate of beating in the EBs may be predicted to have a similar effect on intact human hearts. Likewise, agents which alter the pattern of beating by increasing the pause duration in episodic beating, may be predicted to have propensity to produce heart block in patients.

One problem in the testing of cardiomyocytes in EBs is that the rate of spontaneous beating is variable can be dependent on a variety of factors. Since an objective is to obtain controlled data demonstrating the effect of exogenous substances on cardiomyocyte behavior in EBs, one way to provide a controlled baseline of activity is to artificially regulate the beating of the cardiomyocytes in culture. This can be readily done by applying an electrical field stimulation to the EB. This is done most simply by applying electrodes to opposite sides of the culture container in which the EB is contained. If periodic exciting voltages are applied between those electrodes (e.g. 40 volt DC pulses of 10 microsecond duration at 1 hertz) the EBs will exhibit regular pulsing or beating at the frequency of the electrode stimulation. It is necessary as a part of this process to maintain the EB culture at a constant temperature, since temperature changes can also effect the amplitude of EB beats. It is possible to optically scan the EBs during such beating, using imaging processing observing the EB with video microscopy, to determine the amplitude of the beats which occur in such an EB. It then becomes possible to stimulate the EB with a chemical or other stimulus to observe what effect the stimulation has on the magnitude of the beat produced by the EB. Agents which antagonize electromechanical activity in cardiac cells will reduce the amplitude of such beats and agents which agonize such electricomechanical activity will increase the magnitude of such beats. Additionally other properties of the beat can be monitored such as the rate of contraction and relaxation of the embryoid body providing additional mechanistic information.

Figure 1:
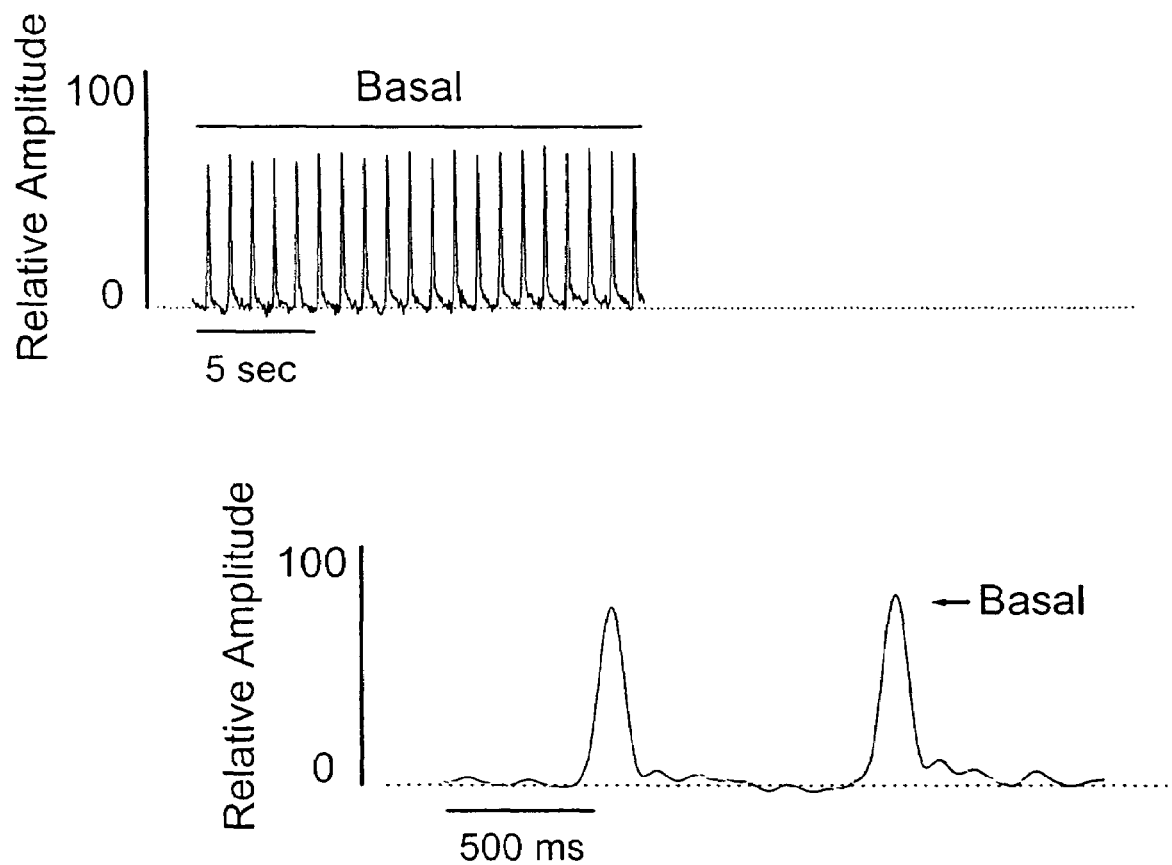
FIG. 1 is a graphical presentation of the amplitude of mechanical contractions occurring in an embryoid body formed from human embryonic stem cells, measured over time to determine the rate of contractions and the amplitude of contractions, gathered in the examples below.

Shown in FIG. 1 is data obtained from such a study. In FIG. 1, an EB is contained within a temperature controlled small culture vessel that has been electrically stimulated at 1 hertz and therefore exhibits a basal amplitude of pulses or beats, the amplitude of which, judged optically by physical displacement of the edge of the EB, is arbitrarily defined to have a control or basal level of 100. Then, a stimulus, such as a test compound, is added to the medium in which the EB is resting which can affect the electrical and mechanical characteristics of a cardiac cell. The chemical stimulant or test compound in this study was the addition of 1 micromolar isoproteranol, which is a known agonist for β-adrenergic receptors in heart cells that can activate an increase in the rate and magnitude of heart contractions. Isoproteranol is known to be a mimic of the "fight or flight" response in adult heart cells. Since the beating rate of the EB is controlled by the rate of the artificially applied field stimulation, the rate of pulsing of the EB does not change, but as shown in FIG. 1, the amplitude of the beat or contraction of the EB increases dramatically upon the application of the chemical stimulus. This demonstrates that chemicals having an effect upon heart contraction can be modeled using cardiomyocytes in culture contained within EBs from embryonic stem cells.

It is also possible to probe the electric action potential characteristics of individual cardiomyocytes in an EB. This is done by creating a very fine microelectrode and physically directing that microelectrode into the EB. While it is not possible to select which cell is probed by that electrode, it is possible to measure the electrical signal experienced by the electrode and determine into what type of cardiomyocyte the probe has been extended based upon the electrical signal created by the cell. This is possible because the different types of heart cells have distinctive electrophysiological properties due to the expression of a unique set of ion channels and other proteins.

Thus an effort was undertaken to characterize the action potentials of cells occurring in beating EBs. These studies were conducted in intact EB outgrowths to avoid the possible alterations in electrical behavior which might arise from cell isolation or replating of isolated cardiac cells. Because the focus of this effort was, in part, to determine if multiple types of cardiomyocytes can be obtained from human embryonic stem cells, the study was conducted on cells in a time window of 40 to 95 days of differentiation of EBs, a time period selected to provide adequate time for distinct cell types to resolve.

Figure 2:
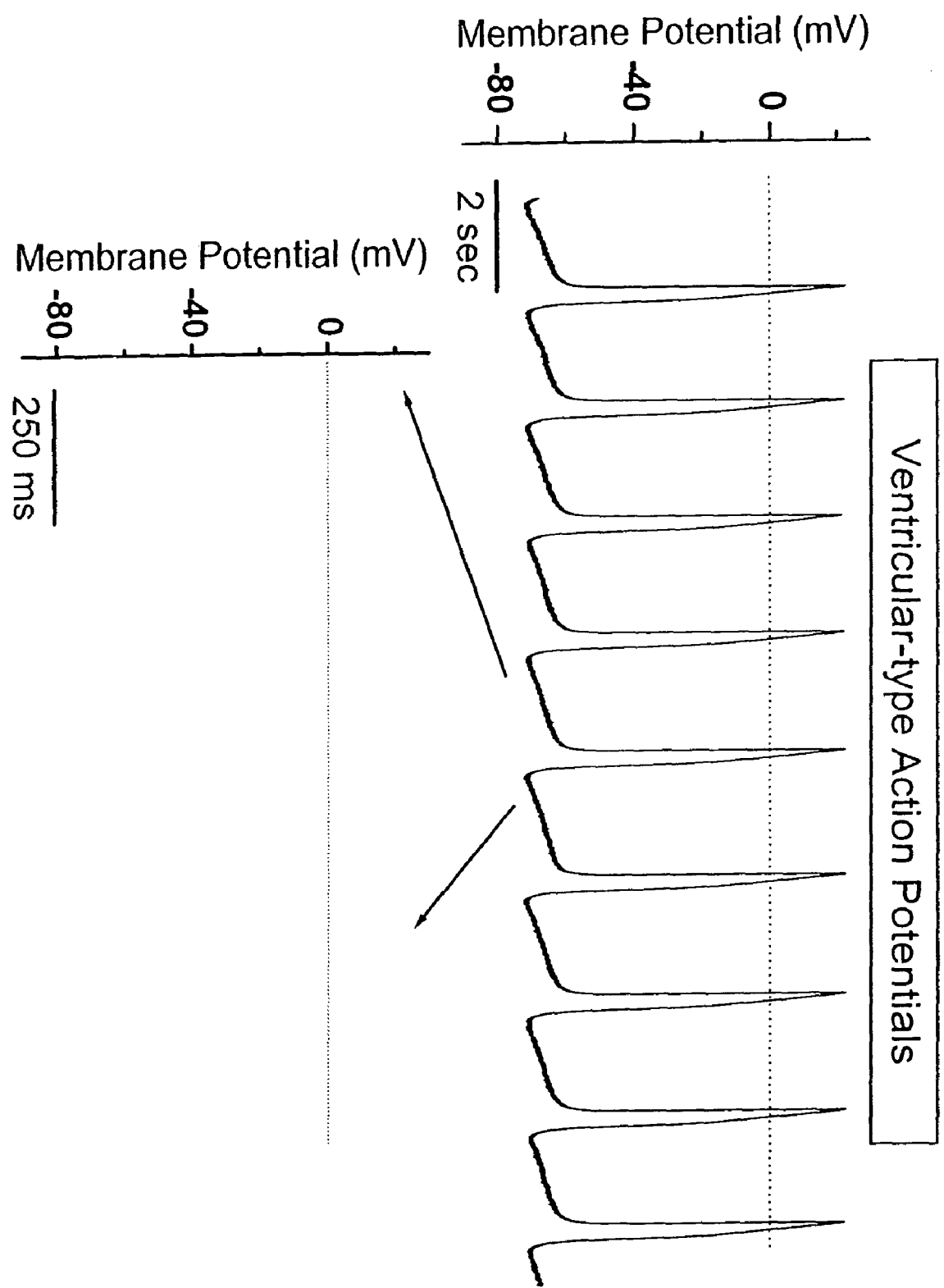
FIG. 2 is a graphical representation of the embryonic ventricular-type action potential observed in cardiomyocytes derived from human embryonic stem cells.
Figure 3:
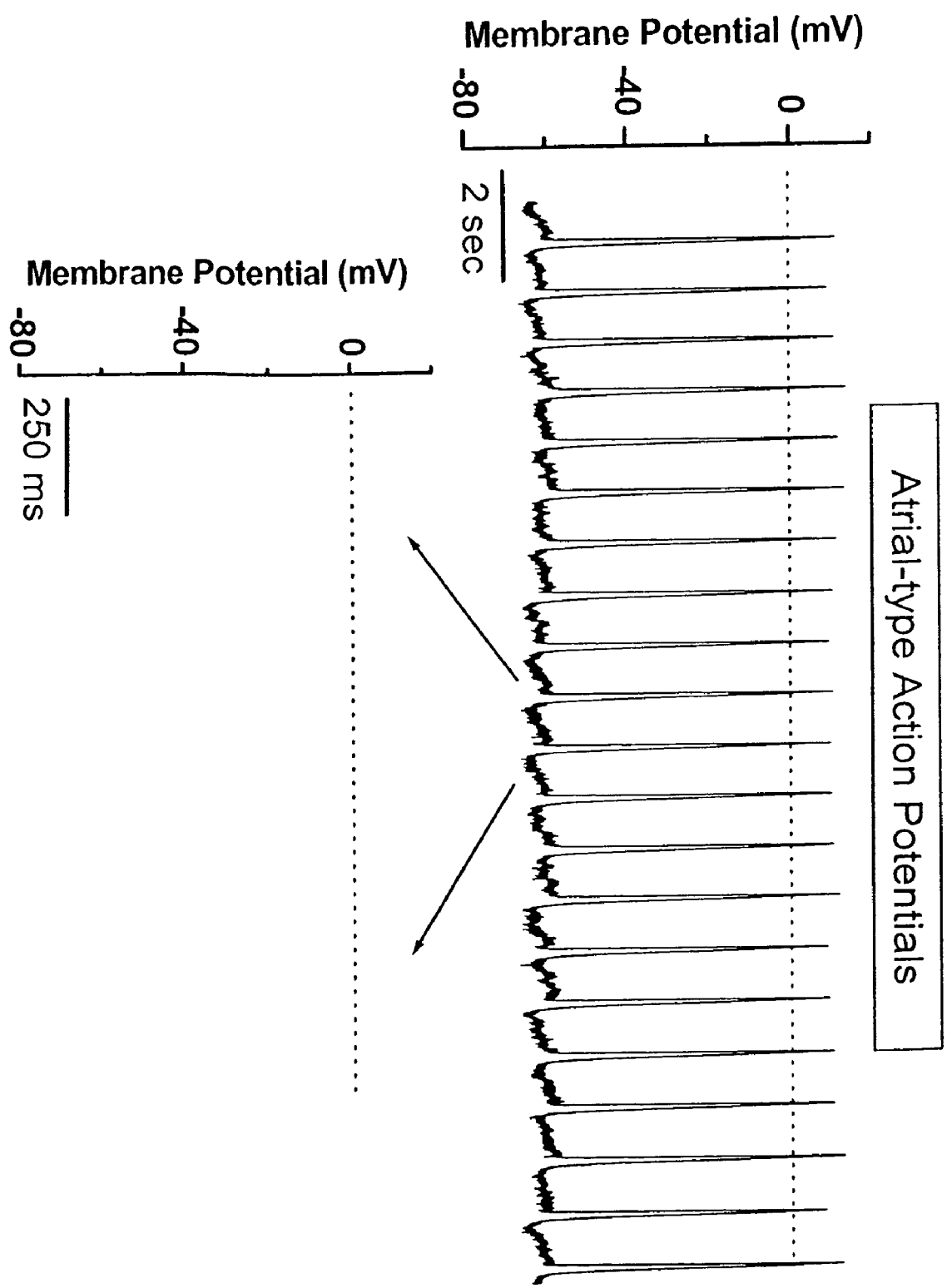
FIG. 3 is a graphical representation of the embryonic atrial-type action potential observed in cardiomyocytes derived from human embryonic stem cells.
Figure 4:
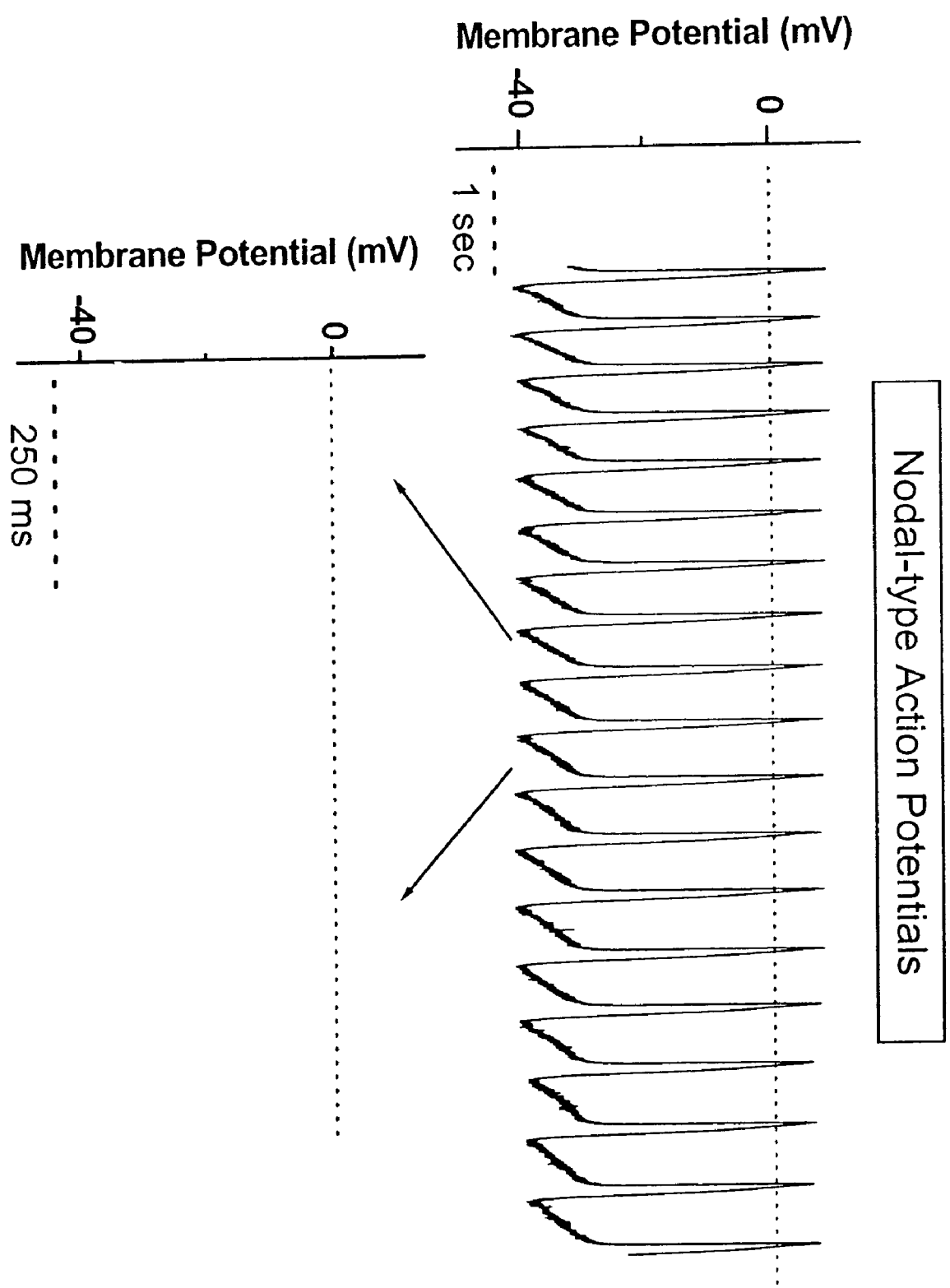
FIG. 4 is a graphical representation of the nodal-type action potential observed in cardiomyocytes derived from human embryonic stem cells.

Shown in FIGS. 2, 3 and 4 are electrical signals obtained from such a probe when placed into different cells in embryoid bodies arising in human stem cell cultures. In FIG. 2, an embryonic ventricular cell type of action potential has been detected. The waveform is characteristic of ventricular cells, as determined by the magnitude and shape of the potentials generated by the cell. In FIG. 3, an embryonic atrial cell type action potential is illustrated. In FIG. 4 a nodal type electrical characteristic is charted. These signals, all taken from actual cardiomyocytes in EBs in culture, are diagnostic of cell type to those knowledgeable in the field of cardiac electrophysiology. These action potentials demonstrate that three major cell types of a mature heart are present among the cardiomyocytes in an EB in vitro culture. Again, it was observed that various beating EBs would have differing predominant cell types, and all three main cell types can be observed.

While it has been proposed before that embryonic stem cell-derived cardiomyocytes might be useful for some forms of drug screening, of particular interest is the effect the potential drugs might have on repolarization (return to baseline) of the action potential. Agents which prolong repolarization, and hence increase action potential duration, have the possibility of causing drug-induced long QT syndrome, which is associated with potentially lethal ventricular arrhythmias. The name QT syndrome is not an abbreviation, it refers to the time interval between points of the action potential chart which are arbitrarily named Q and T. This syndrome represents one of the major forms of toxicity seen across multiple classes of pharmaceutical agents. While modulation of a variety of ion channels can prolong the action potential, in humans the potassium channel known as the HERG channel is particularly susceptible to blockade by drugs, leading to prolongation of the action potential and QT interval on the surface electrocardiogram. Currently no in vitro technique is available for screening for action potential prolongation and HERG channel block in human cardiac myocytes. While a variety of screening approaches are under use to evaluate candidate drugs using animal heart cells and expression of HERG channels in non-cardiac cells, these methods have failed on multiple occasions. In fact, recent history reveals several important pharmaceuticals, notably terfenadine (sold as Seldane™) and astemizole (sold as Hismanal™) which were approved by FDA for marketing but which were subsequently removed from the market when they were found to have adverse effect upon HERG channel activity in human heart cells, because they lead to rare but lethal cardiac arrhythmias in humans. When and if human ES-derived cardiomyocytes would express the HERG channel genes was unknown before the work described here.

The applicants here have determined that the HERG channel response of cardiomyocytes in culture created from human embryonic stem cells can be tested and that they do have the same responsive characteristics as mature heart cells in adult humans. Shown in FIG. 5 is an experiment conducted on an atrial type cell, which is a cardiomyocyte in an EB in culture. Note that the electrical profile of the potential generated by that cell, labeled basal in FIG. 5, is characteristic of an embryonic atrial type action potential. To the culture in which that basal signal was being observed, 500 nanomolar E4031 was added. E4031 is a known highly specific HERG channel blocker which blocks the rapid delayed rectifying potassium current ($I_{Kr}$) in adult human heart cells. The addition of that chemical to the medium in which the EB was cultured led to the modification of the action potential generated by that atrial type cell, as illustrated by the curve marked "500 nM E4031" in FIG. 5. The action potential was prolonged due to delayed return to a resting state. This is precisely the effect that this molecule, E4031, is known to have on adult heart cells and precisely the effect that one would predict from the blockage of the HERG channel. Accordingly, this test demonstrates that it is possible to test molecules for their effect on the HERG channel in adult human cardiac cells by testing cardiomyocytes derived from human embryonic stem cells in culture.

The applicants have determined that the electrical activity of cardiomyocytes in EBs can also display electrical activity known as delayed after depolarizations (DADs). This electrical property is found in diseased human heart muscle or heart muscle treated with agents which cause calcium overload. These DADs serve as the basic mechanisms leading to triggered arrhythmias including some forms of potentially lethal ventricular tachycardia. The ability of EBs to demonstrate the complex cellular environment needed for generation of DADs makes them a suitable model for testing interventions including drugs to modulate DAD formation and potentially derive new pharmacological therapies for heart arrhythmias.

Following here are methods and materials and several examples describing the work conducted with cardiomyocytes derived from human embryonic stem cells. In particular, techniques are described which enable the isolation of large quantities of ventricle type, atrial type or nodal type cells from EBs generated from human embryonic stem cells. This makes possible the collection and culturing of large numbers of such cells for drug screening or other toxicity testing purposes.

EXAMPLES

EB Formation and Cardiac Differentiation

The hES cell lines H1, H7, H9 and H14 were derived and maintained as previously described. For EB formation, ES cell colonies were dispersed into cell aggregates containing approximately 500-800 cells using 1 mg/ml dispase. The cell aggregates were then cultured in suspension in cell culture flasks (BD Bioscience) with ES cell medium without basic fibroblast growth factor for 6 days with media changed daily. To promote cardiac differentiation, 6-day old EBs were transferred to the 6 well plates coated with 0.1% gelatin in media consisting of DMEM supplemented with 15% FBS (selected for cardiac differentiation), 2 mmol/L L-glutamine, and 1% nonessential amino acids. During differentiation, the media was changed daily. Spontaneously contracting cells appeared as clusters in outgrowths from the EBs. These beating EBs were maintained in long-term cultures for up to 95 days.

Immunostaining

Beating foci were isolated with Pasteur pipettes and digested with 0.05% trypsin for 20 min with intermittent vortexing. After cells were centrifuged and resuspended in DMEM medium containing 20% FCS and 0.5% chicken embryo extracts (GIBCO/BRL), cells were plated onto gelatin (0.3%) coated coverglasses and incubated in 10% FCS medium for two days. Immunostaining was done as described elsewhere.

Intracellular Electrophysiology

A single beating, microdissected EB outgrowth was cultured on a glass coverslip for 1-10 days. The coverslip was then attached to the bottom of an experimental chamber mounted on an inverted microscope (Nikon Diaphot 200). The EBs were perfused with Tyrodes solution consisting of (mmol/L): 140 NaCl, 1 MgCl2, 10 HEPES, 10 Glucose, 1.8 CaCl2, pH 7.4 with NaOH at 37° C. Contractions were measured using video edge detection. For intracellular electrophysiology experiments, sharp glass microelectrodes were fabricated with resistances of 30-100 MΩ when filled with 3 mol/L KCl. Spontaneously beating EBs were impaled with the microelectrodes and pipette capacitance was nulled. Intracellular recordings of membrane potential were made using an Axoclamp-2A amplifier in Bridge Mode (Axon Instruments, Foster City, Calif.), and recordings which showed a stable maximum diastolic potential (MDP) for at least 5 minutes were included in data analysis. In some experiments, the preparation underwent electrical field stimulation at rates from 1 to 3 Hz. Data were digitized at 20 kHz and filtered at 2 kHz. APs were analyzed using pClamp8.02 (Axon Instruments, Foster City, Calif.) and Origin 6.0 software (Microcal Inc, Northampton, Mass.) to determine AP duration at 50% and 90% of repolarization (APD50 and APD90), AP amplitude (APA), maximum diastolic potential (MDP), and the maximum rate of rise of the AP upstroke (dV/dtmax).

Contraction Measurements

Contractions were measured using video edge detection. A single beating embryoid body (EB) outgrowth cultured on a glass coverslip was attached to the bottom of an experimental chamber mounted on an inverted microscope (Nikon Diaphot 200). The preparation was continuously perfused with Tyrodes solution containing (mmol/L): 140 NaCl, 1 $MgCl_2$, 10 HEPES, 10 Glucose, 1.8 $CaCl_2$, pH 7.4 with NaOH with additional drugs as indicated. Electrical field stimulation with Grass SD-9 stimulator (Quincy, Mass.) was carried out with two platinum electrodes along opposite walls of the 200-μl experimental chamber (Warner Instrument Corp). The stimulation protocol was from 1 to 3 Hz, 10-ms duration, and 30 to 50 V at 37° C. Individual beating EBs were monitored with Video Edge Detector VED 105 (Crescent Electronics) through CCD BW Camera NL-2332 (National Electronic) and Sony BW Video Monitor PVM-97 (Sony Corp). The twitch responses at sharp edge of beating EB outgrowth were recorded at 1 kHz through DigiData 1200 A/D converter with pClamp 8.2 acquisition software (both from Axon Instrument, Foster City, Calif.). The contractile responses are normalized to basal levels. The experimental chamber temperature was controlled at 37±0.5° C. by Dual Automatic Temperature Controller TC-344B (Warner Instrument Corp).

Cardiac Differentiation in EBs

Our initial studies showed that H1, H7, H9 and H14 ES cell lines can form EBs with spontaneously contracting outgrowths. Beating EBs are first observed approximately 10 days into differentiation and after 30 days approximately 10-25% of EBs show spontaneous contractions. With daily gentle media changes and low EB density, the EBs continued to contract in culture for a period of observation of up to 95 days of differentiation. The remainder of the experiments then focused on EBs derived from H9 and H14 cell lines, and results from these two cell lines were indistinguishable.

Immunostaining was performed to confirm the presence of CMs in the beating EB outgrowths and to examine contractile/sarcomeric protein organization. Beating foci were digested and plated as a monolayer for immunostaining using antibodies against α-actinin, sarcomeric myosin heavy chain (MHC), and cardiac Troponin I (cTnI). Cells isolated from beating foci resumed spontaneous beating after 6-48 hrs plating on coverglasses.

Staining with anti α-actinin antibodies showed varying cytoplasmic patterns ranging from unorganized myofilaments to well organized sarcomeric myofilaments with Z-lines. Sarcomeric MHC staining showed an abundant signal distributed throughout cytoplasm, which is a typical staining pattern with this antibody.

Immunostaining of cTnI showed well-organized parallel myofilament and a striated pattern of I bands in some cells. These observations clearly indicated that cardiac myocytes are present in differentiating EBs and some CMs show significant sarcomeric organization. Although cells were from beating foci, there are non-CMs indicated by nuclear staining but lack of cardiac specific protein immunostaining. The percentage of CMs isolated from beating foci varied widely, ranging from 2% to 70%.

Positive Inotropic Response to β-adrenergic Stimulation

An increase in contractility of cardiac muscle in response to β-adrenergic stimulation requires appropriate surface membrane receptors coupled to a signaling pathway that stimulates a variety of ion channels, membrane transporters and myofilament proteins. However, the responsiveness of cardiac contractility to β-adrenergic stimulation changes over the course of development with the earliest embryonic cardiac myocytes being unresponsive to β-adrenergic agonists. Therefore, we sought to determine if the beating EB outgrowths showed a change in contractile properties in response to the β-adrenergic agonist isoproterenol (Iso). Contractions of the EB outgrowths were measured using video edge-detection techniques during electrical field stimulation to control the beating rate. The magnitude of deflection of the edge of the outgrowth with each stimulated contraction gives a measure of contractility. FIG. 2 demonstrates the contractile pattern of an EB stimulated at 1 Hz under basal conditions and then after superfusion with 1 μmol/L Iso. A clear increase in the magnitude of the contraction is observed, and on average 1 μmol/L Iso resulted in a 33 plus or minus 27% increase in the contraction magnitude (n=5, p=0.05). This measurement showed significant variability from EB to EB in part due to the distinct and complex geometry of each beating outgrowth. These results demonstrate that β-adrenergic receptors are present in human embryonic stem cell-derived cardiomyocytes and stimulation of these receptors produces a positive inotropic response.

Patterns of Spontaneous Electrical Activity

Observations of beating EBs in culture revealed at least two distinct patterns of beating, continuous beating or episodic beating. To investigate this beating pattern further, we made intracellular recordings of action potentials with sharp microelectrodes in twenty spontaneously contracting EBs. Continuous electrical activity was documented in 12/20 EBs. EBs with continuous electrical activity had spontaneous action potential rates that were relatively constant throughout the recording period and ranged between 38 and 106 bpm. In 8/20 EBs, episodic activity was observed, and a clear periodicity of activity was evident. Each burst of activity is characterized by action potentials resuming at a relatively rapid rate that then tapers, followed by another pause. For episodic activity, the duration of active periods and pauses varied from EB to EB, and there was a rough parallel in the duration of spontaneous electrical activity and pauses for each EB.

Multiple Types of Action Potentials

To characterize the types of cardiomyocytes in the EBs, we examined the shape and properties of action potentials from 105 stable impalements of 20 different EBs. At the time window of differentiation that we studied (40-95 days), there was clear heterogeneity in the morphology of the action potentials; however, the action potentials could be classified into 3 major types: nodal-like, embryonic atrial-like, and embryonic ventricular-like (FIGS. 2, 3 and 4). This classification was based on the properties of the action potential as measured by the maximum rate of rise of the action potential (dV/dtmax), the action potential duration (APD), action potential amplitude (APA), and prominence of phase 4 depolarization. Nodal-like action potentials (FIG. 4) were characterized by prominent phase-4 depolarization, slow upstroke (dV/dtmax), and a smaller APA. Embryonic ventricular-like action potentials (FIG. 2) could be distinguished by the presence of a significant plateau phase of the action potential resulting in a significantly longer duration compared to the more triangular shaped embryonic-atrial action potentials. In addition, embryonic ventricular-like action potentials generally showed a trend for slower spontaneous rates of activity the longer the EBs were maintained in culture from 40 to 95 days.

These latter two classes of action potentials are referred to as embryonic, because they have properties more reminiscent of embryonic hearts, which are quite distinct from neonatal and adult cardiac muscle. In particular, the embryonic action potentials are characterized by more depolarized maximum diastolic potentials (MDP) and "slow" type action potentials based on low dV/dtmax (~5-30 V/sec)

To compare action potentials, and hence cardiac cell types in a given EB outgrowth, we made multiple separate impalements with up to 14 separate recordings per outgrowth. Our findings were that multiple intracellular recordings from a single EB are characterized by a predominant action potential phenotype. To provide a quantitative comparison of all of the action potentials recorded from each impalement of a single EB, we plotted the measured APD90s grouped per EB. In general, the APD90s clustered closely together for a given EB but showed variability from EB to EB studied. These results suggest that for any given beating EB outgrowth, spontaneous differentiation favors a predominant cardiac myocyte cell type based on the reproducible action potential morphology observed.

Rate Adaptation of Action Potentials

A fundamental property of cardiomyocytes is the ability to adapt to an increase in heart rate with a decrease in APD. Rate adaptation is present in atrial and ventricular muscle, and it can be impaired in certain disease states. Shortening of APD with rate has also been observed in embryonic (7-12 wk) human ventricular muscle. Therefore, we sought to determine if the embryonic ventricular-like action potentials exhibited appropriate rate adaptation. Isolated EB outgrowths were subjected to electrical field stimulation at three different rates, and steady state action potentials were then recorded and analyzed. An increase in stimulation frequency from 1 to 2 Hz resulted in APD50 and APD90 shortening on average approximately 20% (FIG. 5C), and there was an additional small decrease in APD as the rate was increased to 3 Hz. However, there were no changes in APA or upstroke of the action potential evident at the different stimulation rates tested. These results demonstrate that embryonic ventricular-like cardiomyocytes present in beating EBs have the necessary ion channels and regulatory properties to exhibit rate adaptation. Similar results were also observed for embryonic atrial-like myocytes.

Human Stem Cell-derived Cardiomyocytes have Significant $I_{Kr}$

Repolarization of the cardiac action potential is due to multiple ionic currents with an important role played by voltage gated K+ channels; however, there is significant species variability of the exact type of K+ channels present. In human heart, current through HERG potassium channels (KCNH2), $I_{Kr}$, plays a major role in repolarization of the action potential. HERG channels are also important in drug development as they represent a promiscuous target for drug block that can result in action potential prolongation and the potentially lethal ventricular arrhythmias torsades de pointes. Therefore, we examined the contribution of $I_{Kr}$ to repolarization of action potentials in human embryonic stem cell-derived cardiomyocytes utilizing the HERG specific channel blocker E-4031. Application of 500 nM E-4031 resulted in action potential prolongation in both embryonic atrial and embryonic ventricular-like cardiomyocytes. Prolongation of the AP was most evident for terminal repolarization (phase 3) where HERG current is maximal. In embryonic atrial-like cardiomycytes, APD90 but not APD50 was significantly prolonged, and in embryonic ventricular-like cardiomyocytes significant prolongation of both APD50 and APD90 was produced by E-4031 with a larger effect on APD90. There were not statistically significant effects by E-4031 on APA or MDP. These results suggest that HERG channels are expressed in both embryonic atrial-like and embryonic ventricular-like cardiomyocytes and that $I_{Kr}$ contributes significantly to repolarization of the action potentials in these cell types.

Provoked Early and Delayed After Depolarizations

A major mechanism underlying certain types of cardiac arrhythmias is triggered activity, which results from after depolarizations. These can be divided into early afterdepolarizations (EADs) which occur during the repolarization of the action potential or delayed after depolarizations (DADs) which occur after full repolarization. EADs and DADs result from different cellular mechanisms, but both require a specific and complex set of interacting ion channels and Ca2+ cycling proteins present in cardiac myocytes. Therefore, we examined embryonic ventricular-like cardiomyocytes for the ability to develop EADs and DADs. EADs typically occur in the setting of a prolonged action potential. EADs were defined as depolarizations occurring near the action potential plateau and were observed in ⅗ embryonic ventricular-like CMs treated with E-4031. EADs were never observed in the absence of E-4031. DADs typically occur during Ca2+ overload such as produced by injury or digoxin toxicity. DADs were observed to occur spontaneously in a small number of cells immediately following microelectrode impalement presumably due to injury associated with impalement and associated Ca2+ overload. These cells were not used for characterization of action potential properties, but they demonstrate the ability of the human embryonic stem cell-derived cardiomyocytes to exhibit DADs.

We claim:

1. A method for testing an agent for effect on human cardiac cells comprising the steps of
    culturing aggregates of approximately 500-800 undifferentiated human embryonic stem cells to produce embryoid bodies;
    differentiating the embryoid bodies in in vitro culture for between 40 and 95 days to derive atrial-, ventricular- and nodal cardiomyocyte cell types;
    piercing a single cardiomyocyte with an electrode so that the transmembrane action membrane of that cardiomyocyte can be electrically measured;
    measuring the transmembrane action potential of the single cardiomyocyte;
    assessing the transmembrane action potential of the cardiomyocyte to characterize the cardiomyocyte as to the cell type of the human heart that the action potential most resembles among the cell types selected from the group consisting of ventricular, atrial and nodal cell types;
    exposing the cardiomyocyte to the agent; and
    observing whether the action potential of the cardiomyocyte changes after the exposure to the agent.

2. A method for testing an agent for its effect on the electrical properties of the HERG channel in human cardiac cells comprising the steps of
    culturing aggregates of approximately 500-800 undifferentiated human embryonic stem cells to produce embryoid bodies;
    differentiating the embryoid bodies in in vitro culture for between 40 and 95 days to derive atrial-, ventricular- and nodal cardiomyocyte cell types;
    inserting an electrode into the interior of a single cardiomyocyte in culture in order to be able to measure the transmembrane action potential of the cardiomyocyte;
    measuring the duration of the transmembrane action potential of the cardiomyocyte;
    assessing the transmembrane action potential of the cardiomyocyte to characterize the cardiomyocyte as to the cell type of the human heart that the action potential most resembles among the cell types selected from the group consisting of ventricular, atrial and nodal cell types;
    exposing the cardiomyocyte to the agent; and
    observing whether the action potential duration is changed by the agent, as would be the case if the HERG channel is altered.

3. A method for testing an agent for its likelihood of triggering delayed after depolarization events in human cardiac cells comprising the steps of
    culturing aggregates of approximately 500-800 undifferentiated human embryonic stem cells to produce embryoid bodies;
    differentiating the embryoid bodies in in vitro culture for between 40 and 95 days to derive atrial-, ventricular- and nodal cardiomyocyte cell types;
    inserting an electrode into the interior of a single cardiomyocyte in culture in order to be able to measure the transmembrane action potential of the cardiomyocyte;
    obtaining a chart of the transmembrane action potential of the cardiomyocyte over time;
    assessing the transmembrane action potential of the cardiomyocyte to characterize the cardiomyocyte as to the cell type of the human heart that the action potential most resembles among the cell types selected from the group consisting of ventricular, atrial and nodal cell types;
    exposing the cardiomyocyte to the agent; and
    observing whether a delayed after polarization event is triggered by the agent.

4. A method for testing an agent for its likelihood of triggering long QT syndrome in patients by testing human cardiac cells comprising the steps of
    culturing aggregates of approximately 500-800 undifferentiated human embryonic stem cells to produce embryoid bodies;
    differentiating the embryoid bodies in in vitro culture for between 40 and 95 days to derive atrial-, ventricular- and nodal cardiomyocyte cell types;
    separately inserting an electrode into the interior of several single cardiomyocytes in the culture in order to be able to measure the transmembrane action potential of the cardiomyocytes;
    obtaining a chart of the transmembrane action potential of a plurality of the cardiomyocytes over time;
    assessing the transmembrane action potential of the cardiomyocytes to characterize the cardiomyocytes as to the cell type of the human heart that the action potential most resembles among the cell types selected from the group consisting of ventricular, atrial and nodal cell types;
    exposing the cardiomyocytes to the agent; and
    observing whether action potential duration is prolonged, as an indicator of the risk of long QT syndrome by the agent in any of the cardiomyocytes.

5. A method for testing an agent for effect on human cardiac cells comprising the steps of
    culturing aggregates of approximately 500-800 undifferentiated human embryonic stem cells by in vitro culture to produce embryoid bodies;
    selecting amongst the embryoid bodies for embryoid bodies which demonstrate the presence of atrial-, ventricular- and nodal cardiomyocyte cell types;
    piercing the embryoid body to place a fine electrode inside a single cardiomyocyte within the embryoid body so that the transmembrane action membrane of that cardiomyocyte can be electrically measured;
    measuring the transmembrane action potential of the single cardiomyocyte;
    assessing the transmembrane action potential of the cardiomyocyte to characterize the single cardiomyocyte as to the cell type of the human heart that the action potential most resembles among the cell types selected from the group consisting of ventricular, atrial and nodal cell types;
    exposing the cardiomyocyte to the agent; and
    observing whether the action potential of the cardiomyocyte changes after the exposure to the agent.

* * * * *

UNITED STATES PATENT AND TRADEMARK OFFICE
CERTIFICATE OF CORRECTION

PATENT NO.      : 7,611,852 B2
APPLICATION NO. : 10/627245
DATED           : November 3, 2009
INVENTOR(S)     : Thomson et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 362 days.

Signed and Sealed this

Twelfth Day of October, 2010

David J. Kappos
*Director of the United States Patent and Trademark Office*